US010045935B2

(12) United States Patent
Mikulásik et al.

(10) Patent No.: US 10,045,935 B2
(45) Date of Patent: Aug. 14, 2018

(54) TRANSDERMAL FORMULATION CONTAINING COX INHIBITORS

(75) Inventors: Endre Mikulásik, Körmend (HU); Tamás Spaits, Körmend (HU); Ágota Szakályné Sinka, Szombathely (HU)

(73) Assignee: EGIS PHARMACEUTICALS PLC, Budapest (HU)

( * ) Notice: Subject to any disclaimer, the term of this patent is extended or adjusted under 35 U.S.C. 154(b) by 0 days.

(21) Appl. No.: 13/562,686

(22) Filed: Jul. 31, 2012

(65) Prior Publication Data

US 2014/0037738 A1 Feb. 6, 2014

(51) Int. Cl.
*A61K 47/34* (2017.01)
*A61K 9/14* (2006.01)
*A61K 31/415* (2006.01)
*A61K 31/42* (2006.01)
*A61K 47/46* (2006.01)
*A61K 9/00* (2006.01)
*A61K 31/365* (2006.01)
*A61P 1/04* (2006.01)
*A61P 29/00* (2006.01)
*A61P 1/00* (2006.01)
*A61P 15/00* (2006.01)
*A61P 19/02* (2006.01)
*A61K 47/10* (2017.01)
*A61K 9/06* (2006.01)
*A61K 47/32* (2006.01)
*A61K 31/635* (2006.01)

(52) U.S. Cl.
CPC .............. *A61K 9/0014* (2013.01); *A61K 9/06* (2013.01); *A61K 31/635* (2013.01); *A61K 47/10* (2013.01); *A61K 47/32* (2013.01)

(58) Field of Classification Search
None
See application file for complete search history.

(56) References Cited

U.S. PATENT DOCUMENTS

| | | |
|---|---|---|
| 3,998,973 A | 12/1976 | Carlson |
| 4,831,023 A | 5/1989 | Desai et al. |
| 4,837,019 A | 6/1989 | Deckner et al. |
| 5,122,519 A | 6/1992 | Ritter |
| 5,210,103 A | 5/1993 | Grace et al. |
| 5,374,661 A | 12/1994 | Betlach, II |
| 5,451,405 A | 9/1995 | Bartolone et al. |
| 5,466,823 A | 11/1995 | Talley et al. |
| 5,504,215 A | 4/1996 | Talley et al. |
| 5,508,426 A | 4/1996 | Talley et al. |
| 5,510,496 A | 4/1996 | Talley et al. |
| 5,516,907 A | 5/1996 | Talley et al. |
| 5,521,207 A | 5/1996 | Graneto |
| 5,563,165 A | 10/1996 | Talley et al. |
| 5,698,589 A | 12/1997 | Allen |
| 5,756,109 A | 5/1998 | Burger et al. |
| 5,851,544 A | 12/1998 | Habif et al. |
| 6,007,829 A | 12/1999 | Burger et al. |
| 6,156,781 A | 12/2000 | Talley et al. |
| 6,375,986 B1 | 4/2002 | Ryde et al. |
| 6,361,806 B1 | 5/2002 | Allen |
| 6,413,960 B1 | 7/2002 | Talley et al. |
| 6,589,557 B2 | 7/2003 | Straub et al. |
| 6,592,903 B2 | 7/2003 | Ryde et al. |
| 6,800,297 B2 | 10/2004 | Altreuter et al. |
| 7,138,394 B2 | 11/2006 | Schwarz et al. |
| 7,387,789 B2 | 6/2008 | Klose et al. |
| 7,781,429 B2 | 8/2010 | Schwarz et al. |
| 8,246,976 B2 | 8/2012 | Nguyen |
| 2002/0013300 A1 | 1/2002 | Capelli-Schellpfeffer |
| 2002/0110597 A1 | 8/2002 | Ryde et al. |
| 2003/0104019 A1 | 6/2003 | Hopkins et al. |
| 2003/0161867 A1 | 8/2003 | Lu et al. |
| 2003/0180281 A1 | 9/2003 | Bott et al. |
| 2003/0199537 A1 | 10/2003 | Cannon et al. |
| 2004/0029946 A1 | 2/2004 | Arora et al. |
| 2004/0033267 A1 | 2/2004 | Merisko-Liversidge et al. |
| 2004/0063794 A1 | 4/2004 | Schwarz et al. |
| 2004/0120918 A1 | 6/2004 | Lintner et al. |
| 2005/0032916 A1 | 2/2005 | Deckner |
| 2005/0049291 A1 | 3/2005 | Kumar et al. |
| 2005/0069566 A1 | 3/2005 | Tamarkin et al. |
| 2005/0074487 A1 | 3/2005 | Hsu et al. |

(Continued)

FOREIGN PATENT DOCUMENTS

| | | |
|---|---|---|
| DE | 2704081 A1 | 8/1977 |
| DE | 3805744 A1 | 9/1988 |

(Continued)

OTHER PUBLICATIONS

Karade, Preeti, "Formulation and Evaluation of Celecoxib Gel," http://www.jddtonline.info/index.php/jddt/article/view/148, Journal of Drug Delivery and Therapeutics, May 2012, vol. 2, Issue 3.
Mansour, S., "Preparation and evaluation of topical dibucaine emulsion gels," From Egyptian Journal of Biomedical Sciences, 2007, 24, 1-21.
Mackie et al., "Effect of the interfacial layer composition on the properties of emulsion creams," Journal of Agricultural and Food Chemistry, 2007, 55(14), 5611-5619.
Park et al., "Formulation design and evaluation of a ursolic acid microemulsion delivery system for topical formulation," Yakche Hakhoechi, 2005, 35(4), 233-241.
Moates et. al., "Creaming and oscillation rheology of weakly flocculated concentrated emulsions," Colloids and Surfaces, A: Physicochemical and Engineering Aspects, 2001, 190(1-2), 167-178.
Williams et al., "Scale-up of an oil/water cream containing 40% diethylene glycol monoethyl ether," Drug Development and Industrial Pharmacy (2000), 26(1), 71-77.

(Continued)

*Primary Examiner* — John D Pak
*Assistant Examiner* — Luke E Karpinski
(74) *Attorney, Agent, or Firm* — Knobbe, Martens, Olson & Bear, LLP

(57) ABSTRACT

Disclosed are gel compositions suitable for the topical administration of an active compound having poor solubility and skin penetration, for example, of a COX-2 inhibitor compounds, processes of preparation thereof and methods of use thereof for the treatment of indications treatable by the active compound.

15 Claims, No Drawings

(56) References Cited

U.S. PATENT DOCUMENTS

| | | |
|---|---|---|
| 2005/0096371 A1 | 5/2005 | Krishnan et al. |
| 2005/0158348 A1 | 7/2005 | Schwarz et al. |
| 2005/0202056 A1 | 9/2005 | Hopkins et al. |
| 2005/0255130 A1 | 11/2005 | Vishnupad et al. |
| 2005/0255131 A1 | 11/2005 | Vishnupad et al. |
| 2005/0255133 A1 | 11/2005 | Schwarz et al. |
| 2005/0266061 A1 | 12/2005 | Stinchcomb et al. |
| 2006/0015058 A1 | 1/2006 | Kellogg et al. |
| 2006/0159648 A1 | 7/2006 | Davis et al. |
| 2006/0188557 A1 | 8/2006 | Ikesue et al. |
| 2006/0211688 A1 | 9/2006 | Schwarz et al. |
| 2006/0241175 A1 | 10/2006 | Schwartz et al. |
| 2007/0036731 A1 | 2/2007 | Hirsh et al. |
| 2007/0269393 A1 | 11/2007 | Wepfer |
| 2008/0050461 A1 | 2/2008 | Merisko-Liversidge et al. |
| 2008/0107741 A1 | 5/2008 | Merisko-Liversidge et al. |
| 2008/0226732 A1 | 9/2008 | Merisko-Liversidge et al. |
| 2008/0279949 A1 | 11/2008 | Merisko-Liversidge et al. |
| 2010/0105750 A1 | 4/2010 | Aksamit et al. |
| 2010/0215756 A1* | 8/2010 | Mikulasik et al. ........... 424/490 |
| 2010/0233272 A1 | 9/2010 | Appel et al. |
| 2010/0266692 A1 | 10/2010 | Bloom et al. |
| 2010/0322852 A1 | 12/2010 | Merisko-Liversidge et al. |
| 2010/0322853 A1 | 12/2010 | Merisko-Liversidge et al. |
| 2010/0323014 A1 | 12/2010 | Bloom et al. |
| 2010/0329976 A1 | 12/2010 | Merisko-Liversidge et al. |
| 2012/0004305 A1 | 1/2012 | Miura et al. |
| 2012/0004306 A1 | 1/2012 | Miura et al. |

FOREIGN PATENT DOCUMENTS

| | | |
|---|---|---|
| DE | 4131678 A1 | 10/1992 |
| DE | 19700913 A1 | 7/1998 |
| DE | 10032132 A1 | 1/2002 |
| DE | 102004043112 A1 | 3/2006 |
| EP | 0176217 A1 | 4/1986 |
| EP | 0287322 A2 | 10/1988 |
| EP | 0288734 A1 | 11/1988 |
| EP | 0328806 A2 | 8/1989 |
| EP | 0579455 A1 | 1/1994 |
| EP | 0639372 A1 | 2/1995 |
| EP | 0914082 A1 | 5/1998 |
| EP | 1296679 B1 | 3/2006 |
| FR | 2471778 A1 | 6/1981 |
| FR | 2862871 A1 | 6/2005 |
| GB | 2050160 A | 1/1981 |
| GB | 2144989 A | 3/1985 |
| GB | 2185269 A | 7/1987 |
| JP | H02-145512 | 6/1990 |
| JP | 2004-075592 A | 3/2004 |
| KR | 2001018961 A | 3/2001 |
| WO | WO 84/01710 A1 | 5/1984 |
| WO | WO 95/03805 A1 | 2/1995 |
| WO | WO 95/17162 A1 | 6/1995 |
| WO | WO 95/23596 A1 | 9/1995 |
| WO | WO 96/20699 A1 | 7/1996 |
| WO | WO 96/27372 A1 | 9/1996 |
| WO | WO 97/10196 A1 | 3/1997 |
| WO | WO 97/44008 A1 | 11/1997 |
| WO | WO 97/45123 A1 | 12/1997 |
| WO | WO 98/05299 A1 | 2/1998 |
| WO | WO 98/10768 A1 | 3/1998 |
| WO | WO 98/13017 A1 | 4/1998 |
| WO | WO 98/17252 | 4/1998 |
| WO | WO 98/30244 A1 | 7/1998 |
| WO | WO 98/53795 A1 | 12/1998 |
| WO | WO 99/13855 A1 | 3/1999 |
| WO | WO 99/22703 A1 | 5/1999 |
| WO | WO 99/24000 A2 | 5/1999 |
| WO | WO 99/24006 A1 | 5/1999 |
| WO | WO 99/30678 A1 | 6/1999 |
| WO | WO 2000/007566 A1 | 2/2000 |
| WO | WO 2000/007627 A2 | 2/2000 |
| WO | WO 2000/037040 A1 | 6/2000 |
| WO | WO 2000/059465 A1 | 10/2000 |
| WO | WO 00/64450 A1 | 11/2000 |
| WO | WO 2002/002111 A1 | 1/2001 |
| WO | WO 01/43722 | 6/2001 |
| WO | WO 2001/056576 A1 | 8/2001 |
| WO | WO 2002/017889 A1 | 3/2002 |
| WO | WO 2002/017928 A2 | 3/2002 |
| WO | WO 2002/039960 A2 | 5/2002 |
| WO | WO 2002/041865 A1 | 5/2002 |
| WO | WO 2002/041866 A2 | 5/2002 |
| WO | WO 2003/013462 A1 | 2/2003 |
| WO | WO 2003/055465 A1 | 7/2003 |
| WO | WO 2003/061721 A1 | 7/2003 |
| WO | WO 2003/086331 A2 | 10/2003 |
| WO | WO 2004/092283 A2 | 10/2004 |
| WO | WO 2004/096169 A1 | 11/2004 |
| WO | WO 2005/000248 A2 | 1/2005 |
| WO | WO 2005/007129 A2 | 1/2005 |
| WO | WO 2005/046600 A2 | 5/2005 |
| WO | WO 2006/028863 A1 | 3/2006 |
| WO | WO 2006/031848 A2 | 3/2006 |
| WO | WO 2006/091297 A2 | 8/2006 |
| WO | WO 2006/138035 | 12/2006 |
| WO | WO 2007/051596 A1 | 5/2007 |
| WO | WO 2007/066889 A1 | 6/2007 |
| WO | WO 2007/070983 A1 | 6/2007 |
| WO | WO 2009/007764 | 1/2009 |
| WO | 2009/031318 A1 | 3/2009 |
| WO | WO 2010/089617 | 8/2010 |
| WO | WO 2010103845 A1 * | 9/2010 |

OTHER PUBLICATIONS

Manoj et al., "Creaming and rheology of flocculated emulsions," ACS Symposium Series, 1999, 737(Polysaccharide Applications), 234-251.

Wang et al., "The effect of rheological properties of experimental moisturizing creams/lotions on their efficacy and perceptual attributes," International Journal of Cosmetic Science, 1999, 21(3), 167-188.

Manoj et al., "Characterization of a depletion-flocculated polydisperse emulsion. I. Creaming behavior," Journal of Colloid and Interface Science, 1998, 207(2), 283-293.

Fuehrer et al., "Structural research and manufacturing practice of semisolid preparations," SOFW Journal, 1996, 122(10), 664,666,669-670.

Tiemessen et al., "Probing the microstructure of liquid crystalline surfactant systems; a physicochemical study using the rheometry, DTA and oxygen-17 NMR," Journal of Controlled Release, 1990, 13(1), 73-81.

Mueller-Goymann, "Microstructure of 4-component creams," Acta Pharmaceutica Technologica, 1989, 35(3), 116-20.

Tiemessen et al., "In vitro drug release from liquid-crystalline creams; cream structure dependence," Progress in Colloid & Polymer Science, 1988, 77(Dispersed Syst.), 131-5.

Madsen, W. Soendergaard, "Chlorhexidine," Journal of Hospital Pharmacy, 1969, 26(2), 53-5.

Tichy et al., "Effect of β-(1,3)-glucan on rheological properties and stability of topical formulations," Pharmazie, 2006, 61(12), 1050-1051.

Biruss et al., "Evaluation of an eucalyptus oil containing topical drug delivery system for selected steroid hormones," International Journal of Pharmaceutics, 2007, 328(2), 142-151.

Csoka et al., "In vitro and in vivo percutaneous absorption of topical dosage forms: case studies," International Journal of Pharmaceutics, 2005, 291(1-2), 11-19.

Csoka et al., "In vitro drug release and in vivo percutaneous absorption studies of topical dosage forms," Farmacevtski Vestnik, 2003, 54(Spec. Issue), 347-348.

Nour et al., "Formulation and evaluation of econazole nitrate emulgels," Journal of Drug Research, 2002, 24(1-2), 63-71.

El Laithy et al., "The development of cutina lipogels and gel microemulsion for topical administration of fluconazole," AAPS PharmSciTech (2002), 3(4).

Huhtala et al., "A Collaborative Evaluation of the Cytotoxicity of Two Surfactants by Using the Human Corneal Epithelial Cell Line and the WST-1 Test," Journal of Ocular Pharmacology and Therapeutics, 2003, 19(1), 11-21.

(56) References Cited

OTHER PUBLICATIONS

Schlesinger, Marcia, "Topical aerosol foam formulations," Cosmetics & Toiletries, 2000, 115(8), 67-70.
Memisoglu et al., "In vivo evaluation for rhGM-CSF wound-healing efficacy in topical vehicles," Pharmaceutical Development and Technology, 1997, 2(2), 171-180.
Wang et al., "Effect of various physical/chemical properties on the transdermal delivery of cyclosporin through topical application," Drug Development and Industrial Pharmacy, 1997, 23(1), 99-106.
Tous et al., "Acetazolamide topical formulation and ocular effect," S.T.P. Pharma Sciences, 1992, 2(1), 125-31.
Wepierre et al., "Irritant effects of surface active agents evaluated by measuring skin blood flow in the guinea pig," Labo-Pharma—Problemes et Techniques, 1977, 25(264), 300-3.
Modi et al., "A comparative solubility enhancement profile of valdecoxib with different solubilization approaches," Indian Journal of Pharmaceutical Sciences, 2007, 69(2), 274-278.
Abou-Taleb et al., "Formulation and stability of rofecoxib suppositories," Journal of Drug Delivery Science and Technology, 2006, 16(5), 389-396.
Lu et al., "Transdermal and lymph targeting transfersomes of vincristine," Yaoxue Xuebao, 2007, 42(10), 1097-1101.
Junyaprasert et al., "Transdermal delivery of hydrophobic and hydrophilic local anesthetics from o/w and w/o Brij 97-based microemulsions," Journal of Pharmacy & Pharmaceutical Sciences, 2007, 10(3), 288-298.
Valiveti et al., "Transdermal permeation of WIN 55,212-2 and CP 55,940 in human skin in vitro," International Journal of Pharmaceutics, 2004, 278(1), 173-180.
Lee et al., "Evaluation of various vehicles and O/W microemulsions of flurbiprofen as transdermal delivery system," Yakche Hakhoechi, 1998, 28(3), 141-149.
Bodde et al., "Hydrogel patches for transdermal drug delivery; in vivo water exchange and skin compatibility," Journal of Pharmacy and Pharmacology, 1989, 41(3), 152-5.
International Written Opinion for International Application No. PCT/HU2008/000083, Date of Opinion issuance Jan. 10, 2010, 13 pages.
International Preliminary Report on Patentability for International Application No. PCT/HU2008/000083, Date of Preliminary Report issuance Jan. 10, 2010, 14 pages.
Hungarian Office Action for Hungarian Patent Application No. HU20070000473 dated May 9, 2012.
English Translation of Hungarian Office Action for Hungarian Patent Application No. HU20070000473 dated May 9, 2012.
Notice on the Publication of the Patent Application and the Completion of a Novelty Search for Hungarian Patent Application No. HU20070000473 dated on Sep. 23, 2009.
English Translation of Notice on the Publication of the Patent Application and the Completion of a Novelty Search for Hungarian Patent Application No. HU20070000473 dated on Sep. 23, 2009.
Lieberman, H.A., "Pharmaceutical dosage forms: disperse systems," 1996, Edition 2, vol. 2, p. 251.
Dorland's Medical Dictionary for Healthcare Consumers, 2007, Elsevier, Definition of "transdermal" in 1 page.

\* cited by examiner

TRANSDERMAL FORMULATION CONTAINING COX INHIBITORS

The present invention is related to transdermal formulations containing COX-inhibitors. Transdermal formulations, e.g., gels, are important and useful for delivering pharmaceutical formulations. Such formulations offer a possibility for administering medicines to patients who have difficulty in swallowing oral formulations or in cases when prolonged parenteral medication should be replaced. Such formulations furthermore offer the possibility of localized administration of the medicament thus preventing side effects and are suitable for the administration of active ingredients which are metabolized rapidly and extensively subsequent to oral administration. Especially there is a need for transdermal gel formulations that deliver active compounds that are anti-inflammatory and/or pain relieving pharmaceutically active compounds, e.g., COX inhibitors, or selective COX inhibitors, e.g., COX-2 inhibitors, preferably, celecoxib, deracoxib, valdecoxib, rofecoxib, tilmacoxib, or other similar known compounds, especially celecoxib, including its various known crystalline forms and various salts thereof, e.g., crystalline forms I, II, III, IV and N. Additionally important is that the formulation exhibit suitable skin penetration to achieve the required therapeutical objective and advantageous organoleptic properties, such as suitable consistency without adherence (sticking) to the skin or clothing. There is furthermore a need for the formulation to have good physical-chemical stability, especially in the cold, and microbiological stability. In case of low-solubility active ingredient, such as celecoxib, the formulation should also improve the solubility of the active ingredient. Moreover, said formulations should be easily manufacturable on an industrial scale.

Transdermal pharmaceutical formulations are characterized by the measurement of the skin penetration of the active ingredient. Such a measurement method and apparatus developed are disclosed in WO2010089619.

The drugs preferred in the formulations according to the present invention are selective COX-2 inhibitors, which are known to be useful for treating: inflammation, colorectal polyps (because they have effects on abnormally dividing cells such as those of precancerous colorectal polyps), menstrual cramps, sports injuries, osteoarthritis, rheumatoid arthritis, and pain, e.g., acute pain, and for reducing the risk of peptic ulceration. The embodiments of the invention are suitable for use with crystalline or amorphous forms of active ingredients. The preferred drug of the formulations is Celecoxib, which is a selective COX-2 inhibitor having about 7.6-times higher affinity towards COX-2 than towards COX-1. Thus the antiinflammatory activity of celecoxib is only rarely accompanied with gastrointestinal side effects which are often experienced with non-selective non-steroidal antiinflammatory active ingredients.

The invention also includes the use of the formulations for the indications known for the active ingredient. For example, a method of treating inflammation, colorectal polyps, menstrual cramps, sports injuries, osteoarthritis, rheumatoid arthritis, and pain, e.g., acute pain, and of reducing the risk of peptic ulceration, by administering a composition disclosed herein topically is included in the invention.

The delivery of COX-2 inhibitors, especially topically, has many challenges, as these compounds have a very low solubility, high melting point, and low penetration potential in known topical formulations that have acceptable organoleptic (sensory) characteristics. Organoleptic characteristics of importance are: appearance, consistency, viscosity, odour, spreadability, and non-sticking property.

For example, during the reproduction of the experiments of Soliman and co-workers (S. M. Soliman, N. S. Abdel-Malak, O. N. El-Gazayerly, A. A. Abdel-Rehim: Formulation of microemulsion gel systems for transdermal delivery of celecoxib: In vitro permeation, anti-inflammatory activity and skin irritation tests. [Drug Disc & Ther. 2010; 4(6): 459-- - 471.], although technically a gel was obtained, the product was not suitable for product development due to thermal instability and unsatisfactory consistence due to high stickiness.

Applicants have found a solution to the above discussed challenges to the topical delivery of COX-2 inhibitors by the use of a formulation that has excellent organoleptic (sensory) characteristics, while also providing for good skin penetration. Such formulation contains the following ingredients in the following amounts (the amounts and percentages of amounts discussed in the present application are by weight based on the composition as a whole unless indicated otherwise):

I) an active compound, e.g., a COX inhibitor, preferably a COX-2 inhibitor, e.g., celecoxib, deracoxib, valdecoxib, rofecoxib, and/or tilmacoxib, especially celecoxib, and particularly preferably a crystalline form thereof. The active ingredient is preferably in a particulate form, preferably, in micronized form; however, it is possible to produce delivery systems according to the present invention wherein the active ingredient is partly or fully dissolved.

In some embodiments, the particle size of the active ingredient, for example, of celecoxib, is smaller than 5 µm, usually 1-3 µm. The active ingredient does not have to be micronized, but in preferred embodiments, micronized forms are advantageous to further enhance the solubility of the active ingredient.

The amount of active compound, e.g., of celecoxib, should be 0.5-10%, preferably 1-6%, more preferably 1.5-5%, and especially preferably about 2%.

II) a compound or a natural mixture capable of enhancing the penetration of the active ingredient, e.g. celecoxib, including but not limited to menthol, thymol, essential oils such as lavender oil or kernel oils, such as almond oil and vegetable oils etc.

Terpene compounds may also be useful as penentration enhancers, such as isoborneol, irone, ocimene, carveol, carvotanacetone, carvomenthone, carvone, carene, carone, camphene, camphor, geraniol, cymene, sabinene, safranal, cyclocitral, citral, citronellal, citronellic acid, citronellol, cineole, sylvestrene, thujyl alcohol, thujone, terpineol, terpinene, terpinolene, tricyclene, nerol, pinene, pinocampheol, pinol, piperitenone, phellandral, phellandrene, fenchene, fenchyl alcohol, perillyl alcohol, perillyl aldehyde, borneol, myrcene, menthol, menthone, ionol, ionone, linalool, or limonene. Essential oils containing such compounds can also be used.

Considerations in the selection of the compound, an essential oil or natural mixture should be concerns of allergies, aroma, e.g., bad smell versus pleasant smell, the potential of the compound to irritate the skin, potential in causing adverse effects etc. Preferred among the options is menthol and lavender oil, especially menthol.

The amount of the penetration enhancing compound e.g., of menthol or lavender oil, especially menthol, is 0.5-10%, preferably 0.7-5%, more preferably 1-2%, and especially preferably about 1%.

III) a solubilizer, or preferably a solubilizer system having at least two solubilizer components.

Solubilizers are well known in the state of the art. Applicants have found that in the formulation according to the present invention, the solubilizers can be preferably selected from polyethylene glycols, sorbitol esters with fatty acids, pegylated sorbitol esters with fatty acids (polysorbates), polyethylene glycol alkylethers, polyoxyethylene and polyoxypropylene block polymers and silicone alkyl glycols.

When a solubilizer system having at least two solubilizer components is used, the ability of the system is generally significantly improved over the use of a single solubilizer. Solubilizers having large hydrophilic-lipophilic balance (HLB) values, i.e., above 10, preferably above 12, e.g., 13, and more preferably about 14-20, have been found to be particularly useful. As an example, the solubilizers Tween 60, Brij-58, Kolliphor P-407 can be used as a single solubilizer in the formulation according to the present invention.

Applicants have found that a solubilizer known as Brij 58, also known as polyethylene glycol hexadecyl ether or polyoxyethylene (20) cetyl ether, is particularly suitable for the solubility enhancement of COX-2 inhibitor compounds, especially of celecoxib.

The amount of Brij 58 is in the range of 3-25%, preferably 4-15%, more preferably 5-10%, and especially preferably about 7%.

In one embodiment of the invention, the solubilizer used in the formulation is Brij 58.

It is particularly advantageous to use of the combination of Brij 58 with Kolliphor P407, which is also known as Poly(ethylene glycol)-block-poly(propylene glycol)-block-poly(ethylene glycol). Said combination results in an increase in the stability of the formulation, and is unexpectedly better than other solubilizers alone or in combination, for example, the combination of tween 60 and ethanol. Further advantageous combinations of solubilizers include but are not limited to the combination of polyethylene glycol 1000 (PEG 1000) and Brij 58 and PEG 1000, Brij 58 and Kolliphor P407.

Alternate combinations include Tween 60, which is also known as Polyoxyethylene (20) sorbitan monostearate, with either Brij 58 or Kolliphor P407, or other combinations where both solubilizers have HLB values above 10, preferably above 12, e.g., 13, and more preferably about 14-20.

An additional advantage of Kolliphor P407 is its ability to act as a thickening agent and/or gel binder.

Solubilizers that may be included in the solubilizer system are span 60, emulsifier 10, Some of the solubilizers known from the prior art have been found inadequate alone in enhancing the solubility of the active compounds to the desired extent, but may provide some benefit when in combination with a solubilizer having a high HLB value.

When a combination of solubilizers is used, the amount thereof can be the same as when used alone. As such, the amount of Brij 58 in the solubilizer system is the same as when used alone.

The amount of each of the solubilizers in the system can be the same. For example, the amount of Kolliphor P407 in the combination or even when used alone is in the range of 3-25%, preferably 4-15%, more preferably 5-10%, and especially preferably about 7%. The ratio by weight of the solubilizers, for example, when two are present, can be from 1:10 to 10:1, preferably 1:5 to 5:1, more preferably 1:2 to 2:1, and especially preferably 1:1.

The combination of Kolliphor P407 and Brij 58, for example, in a 1:1 mixture results in increased stability.

IV) a wetting agent or lubricant, e.g., Polyethylene glycol (PEG). Preferred among the PEGs is PEG 1000. However, any PEG 200 to PEG 20,000 may be used. Preferably polyethylene glycol are those having a molecular weight equal or less than 1000 and are liquids or of semisolid state.

PEG 1000 improves the handling properties of the ingredients of the formulation which can be dissolved in PEG 1000 even in cold temperatures. However, increasing the concentration of PEG 400 from, for example, 10% to 20% neither improves stability nor membrane penetration, and therefore PEG was believed to be not regardable as a solvent, e.g., true solubilizer, in the formulations of the invention. The unexpected increase in the solubilizing effect and membrane penetration is the likely the result of the addition of the combination of Kolliphor P407 and Brij 58, which may be even further enhanced, e.g., by PEG or other solubilizers and/or wetting agents, and/or the permeation enhancing component, such as menthol.

As such, the use of solubilizers, for example, Brij 58, Kolliphor P407, and PEG 1000 (wetting agent), is preferred for the in vitro penetration of the active ingredient due to its low solubility. The combination of these three agents result in unexpectedly improved in vitro penetration of the active ingredient over other solubilizers, especially when used alone.

PEG in addition to serving as a wetting agent, also appears to be at least partially responsible for enhancing the solubility of the active ingredient, e.g., of celecoxib.

The amount of PEG, preferably of PEG 1000, is in the range of 2-25%, preferably 5-20%, more preferably 8-15%, and especially preferably about 10%.

Other wetting agents in addition or alternate to PEG may be used as long as they provide comparable results to PEG in the composition.

V) a gel forming or thickening agent, preferably Carbopol compounds, preferably Carbopol 980, also known as polymerized prop-2-enoic acid ester. Carbopol 980 is a polymer that is a highly efficient thickener and is ideal for formulating clear aqueous and hydroalcoholic gels. Other gel forming agents known from the state of the art are possible in addition to or alternate to Carbopol 980.

The amount of gel forming agent can be low, as long as sufficient to provide for the formation of a gel, for example, for Carbopol 980 the amount is in the range of 0.1-2%, preferably 0.2-1.5%, more preferably 0.3-1%, and especially preferably about 0.5%.

VI) optionally a precipitation agent or pH adjuster, e.g., a sodium hydroxide aqueous solution, provided that such an agent is required for setting a suitable pH range or precipitation of the gel in conjunction with a specific gel forming agent. Additional or alternate precipitation agents may be useful in the formulations. For example, when a Carbopol gel forming agent is used, it is necessary to use the precipitation agent sodium hydroxide (NaOH) in order to obtain a gel. In case of other gel forming agents, a different precipitating agent known from the state of the art may be necessary. In case of some gel systems, no precipitation agent is required.

The strength of the precipitation agent or pH adjuster solution can vary, but is preferably 10 m/v %.

The amount of precipitating agent should be sufficient to bring about a pH of 5.5-7.5 for the gel forming agent swollen in water, and is typically in the range of 0.5-2%, preferably 0.7-1.5%, more preferably 0.8-1.2%, and especially preferably about 1%.

VII) a volatile siloxane coating agent, or preferably a siloxane coating agent system having at least two volatile siloxane coating agent components, which are used to coat the active ingredient particles. The siloxane coating agent should be highly volatile to be able to evaporate from the skin upon application.

WO2009007764 and WO2010089617 disclose transdermal gel formulations, which are dispersions of solid active ingredient particles coated with a highly volatile siloxane in aqueous gels. The siloxanes disclosed in these applications, i.e., hexamethyldisiloxane, octamethyltrisiloxane and decamethylcyclopentasiloxane, are useful in the present invention for the coating of active compound particles. Other compounds capable of coating a particulate ingredient and evaporating upon application to the skin are also useful instead of the above siloxane compounds. Particularly advantageous volatile siloxanes for coating the particles of the active ingredients are apolar, non-functionalized siloxanes, i.e. they do not contain any polar functional group.

Particularly preferred is a combination of hexamethyldisiloxane and decamethylcyclopentasiloxane. As such, in a preferred embodiment, the formulation contains Silicone Fluid 0.65 cSt (hexamethyldisiloxane) and St-cyclomethicone 5 NF (decamethylcyclopentasiloxane).

Embodiments including St cyclomethicone 5-NF have improved organoleptic properties.

The amount of Silicone Fluid 0.65 cSt when used in the combination and even when used alone is in the range of 1-25%, preferably 5-20%, more preferably 8-15%, and especially preferably about 10%.

The amount of St-cyclomethicone 5 NF when used in the combination and even when used alone is in the range of 1-25%, preferably 3-15%, more preferably 4-10%, and especially preferably about 5%.

The amount of siloxane used should be sufficient to adequately coat either the active ingredient particles to avoid their intermixing with the gel matrix containing solubilizers and penetration enhancing components before the evaporation of the siloxane coating. Too low an amount could lead to the precipitation of the active ingredient particles thus lowering skin penetration The ratio by weight of the siloxane coating agents, for example, when two are present, can be from 1:10 to 10:1, preferably 1:5 to 5:1, most preferably 1:2 to 2:1, including 1:1.

VIII) and finally, purified water added to achieve 100%.

In some embodiments, the above formulation will include additional solvents to water, for example, various alcohols, etc.

Additional ingredients in the composition are possible, as long as they do not negatively affect the effectiveness or organoleptic characteristics thereof. For example, the composition may additionally contain colorants, fragrances, additional cosmoceuticals or nutriceuticals. Such compounds are known from the prior art.

In one embodiment, the composition of the invention contains
a selective COX-2 inhibitor compound,
at least one compound capable of enhancing the skin penetration of the active ingredient,
at least one solubilizer, which is Brij 58,
at least one wetting agent,
at least one gel forming agent,
at least one precipitating agent,
at least one volatile siloxane coating agent, and
at least one solvent.

A preferred composition of the invention contains

| | |
|---|---|
| Celecoxib | 0.5-10% |
| Menthol | 0.5-10% |
| Brij 58 | 3-25% |
| Kolliphor P407 | 3-25%, however, this ingredient may be absent, |
| PEG 1000 | 2-25% |
| Carbopol 980 | 0.25-2% |
| NaOH aqueous solution (10 m/v %) | 0.1%-5% |
| Silicone Fluid 0.65 cSt | 1-25% |
| St-cyclomethicone 5 NF | 1-25% |
| Purified water | ad 100% |

A more preferred composition, which is preferably a solution gel, contains

| | |
|---|---|
| Celecoxib | 2% |
| Menthol | 1% |
| Brij 58 | 7% |
| Kolliphor P407 | 7%, however, this ingredient may be absent, |
| PEG 1000 | 10% |
| Carbopol 980 | 0.5% |
| NaOH aqueous solution (10 m/v %) | 1% |
| Silicone Fluid 0.65 cSt | 10% |
| St-cyclomethicone 5 NF | 5% |
| Purified water | ad 100%. |

A more preferred composition, which is preferably a suspension gel, contains

| | |
|---|---|
| Celecoxib | 2% |
| Menthol | 1% |
| Brij 58 | 5% |
| PEG1000 | 10% |
| Carbopol 980 | 0.5% |
| NaOH solution 10% | 1% |
| Silicone 0.65 cSt | 5% |
| Silicone Cyclomethicone 5-NF | 5% |
| Purified water | ad 100%. |

The amounts indicated herein may be varied for each ingredient, for example, by 20%, more preferably by 10%.

In the above formulations, the menthol may be exchanged for lavender oil or almond oil, for example.

In the above formulations, one or both of Silicone Fluid 0.65 cSt and St-cyclomethicone 5 NF may be used, preferably both.

The formulations may be either in the form of a solution gel, where the active ingredient is dissolved in the gel, or a suspension/dispersion gel, where the active ingredient is in a particulate form suspended and dispersed in the gel. It is possible, however, to produce a formulation wherein the active ingredient is present partly in a solution and partly in suspension gel form at the same time. In such formulations, the proportion of the active ingredient present in suspension (i.e. in particulate form) can be chosen freely.

In the case of suspension gels, the solid particles of active ingredient are coated with one or more siloxanes and dispersed in the gel, thus obtaining a transdermal formulation having similar properties to the solution gels according to the present invention, for example, cold stability and good skin penetration, but providing additional benefits, e.g., even further enhanced stability, e.g., storage stability, especially physicochemical and microbiological stability.

When the gel containing celecoxib particles coated with siloxanes (i.e., a dispersion gel as opposed to the solution gel) is spread onto the skin or other body surface, the temperature of the formulation would increase to, for example, between 24 to 32° C., the volatile siloxanes evaporate. During the course of the evaporation of the volatile siloxanes, the formulation becomes a solution (i.e. particles of celecoxib are solubilized, dissolved) and the solution is absorbed by the skin. Thus, during the course of evaporation after application to the skin, the pharmaceutical form is changed from a suspension into a solution gel.

In preferred embodiments of the present invention, the particles of active ingredient, e.g., celecoxib, are surrounded by a volatile siloxane coating. In this coating, none of the active ingredient, the solubilizing agents, and the gel are soluble. Thus, the physical form of suspension is maintained even though by direct contact, celecoxib would dissolve in the solubilizer, and the formulation is even more stable than when the active compound would be dissolved.

As soon as the formulation is transferred to the skin and the volatile siloxane coating evaporates, the barrier for dissolution disappears, and the active ingredient is contacted with and dissolved in the excipients, especially the solubilizers. Such a change in physical form of the formulation enhances absorption and skin penetration. This formulation thus exhibits controlled release as well as controlled absorption of the active ingredient.

In a preferred embodiment using celecoxib as the active ingredient in a suspension-type gel, the gel base is created from a Carbopol 980, water, and NaOH solution (Carbopol: an acrylate-type gel forming copolymer). Menthol is provided for enhancing the penetration of the active ingredient after the evaporation of the siloxanes and serves also as fragrance. Brij 58 and Kolliphor P407 function as solubilizers and PEG 1000 functions as a wetting agent. Finally the siloxane coating agents used are SF 0.65 and SNF.

In general, the compositions can be prepared by a process that includes swelling the at least one gel forming agent in the at least on solvent, and if required, neutralizing with the at least one precipitating agent until pH 5.5-7.5, or otherwise producing a gel base, warming up the at least one solubilizer to approximately 50° C. and dissolving therein the at least one wetting agent and the at least one compound capable of enhancing the penetration of the active ingredient, thereby forming a melt, stifling the melt into the gel, if more than one, then mixing together the siloxane coating agents, the selective COX-2 inhibitor compound, optionally in micronized form (d90<5 µm), is dispersed in the at least one siloxane coating agent and homogenized, optionally by a colloid mill, thereby forming a suspension, and the suspension is stirred into the gel and homogenized, optionally by a colloid mill, wherein the process includes the interchanging of the at least one compound capable of enhancing the penetration of the active ingredient and the selective COX-2 inhibitor compound in the above process steps.

In a preferred embodiment, the method of manufacture for the suspension formulation is as follows:

i) Carbopol 980 is allowed to swell in the water and neutralized by the NaOH solution until pH 5.5-7.5, thereby forming a gel.

ii) Brij 58 and Kolliphor P407 are warmed up to approximately 50° C. and PEG-1000 and menthol are dissolved in their mixture, thereby forming a melt.

iii) The melt is slowly stirred into the gel.

iv) The two siloxane components are mutually dissolved (i.e., mixed).

v) Micronized celecoxib (d90<5 µm) is dispersed in the mixture of the siloxanes and homogenized, preferably by using a colloid mill.

vi) The suspension of the active ingredient in the siloxanes are stirred into the gel and homogenized, preferably by a colloid mill.

In the case of solution gels, the active ingredient is in a dissolved state in the gel, which contains the solubilizers. No particles of the active ingredient are present. However, in a preferred embodiment, the menthol (which is used as penetration enhancer for the active ingredient, e.g., celecoxib) is coated with the siloxanes.

To achieve said embodiment, in the processing method discussed above instead of the active agent being dissolved in the siloxanes, the menthol used as penetration enhancer is dissolved in the siloxanes, and the active compound is dissolved in the solubilizers. Thus, the gel mixture does not contain a mixture of menthol and the active ingredient. Said mixture is formed in situ after application (onto the skin), i.e., after the volatile siloxanes evaporate the menthol is released into the gel that already contains the dissolved active ingredient.

The formulations of the invention can be administered by the use of a patch. However, preferably, no patch is utilized.

The formulation of the invention, preferably omit the use of higher alcohols and esters thereof, e.g., of saturated or unsaturated higher aliphatic alcohols having 8 to 22 carbon atoms.

Evaluation of membrane penetration is measured by static Hanson-cell with closed membrane surface, acceptor phase is an aqueous buffer, where the sample is deposed on the membrane. The results are given as a cumulative amount of the active ingredient during a 6-hour testing period penetrating the membrane, expressed in micrograms/square centimeters. The membrane used for penetration testing was a cellulosic mixed ester membrane and the acceptor phase was phosphate buffer.

Production of the solution-type gels is carried out in an essentially similar way to that of the suspension/dispersion type gels with small modifications. The active ingredient, e.g. celecoxib is dissolved in the solubilizer-wetting agent mixture heated to approx. 50° C. The siloxane ingredient and the penetration enhancing component, e.g. menthol are dispersed in the gel base prepared according to the method described above and homogenized, for example, using a colloidal mill. Finally, the solution of the active ingredient in the solubilizer-wetting agent mixture is stirred into the gel base and homogenized, e.g. using a colloidal mill.

EXAMPLES

Reference preparations have been produced according to the method disclosed in WO2009007764 by coating the particles of the active ingredient with a volatile siloxane.

Example 1 provides a solution gel formulation of the active ingredient prepared by a process described above.

Example 1

| Celecoxib | 2% | active ingredient |
|---|---|---|
| Menthol | 0.66% | penetration enhancer |
| Brij 58 | 7% | solubilizer |
| Kolliphor P407 | 7% | solubilizer |
| PEG1000 | 10% | wetting agent |
| Carbopol980 | 0.5% | gel-forming agent |
| NaOH solution 10% | 1% | precipitating agent |
| Silicone 0.65 cSt | 5% | siloxane additive |
| Purified water | ad 100% | base, solvent |

Properties:

White gel of excellent consistency with menthol odour and with a membrane penetration (6 hours) of 1398 micrograms/square cm.

Evaluation:

A gel containing the active ingredient is solubilized form. It can be easily manufactured on an industrial scale. The membrane penetration is good, as well as the consistency and organoleptic properties.

The active ingredient has been micronized using a Fritsch Pulverisette 14 milling equipment. Starting particle size was 30-50 μm, and the micronized particle size was 1-3 μm. There is no crystallization. The resulting composition has excellent consistency and applicability. The in vitro membrane penetration is immediate.

Example 2 provides a dispersion gel formulation of the active ingredient prepared by a process described above.

Example 2

| Celecoxib | 2% | active ingredient |
|---|---|---|
| Menthol | 1% | penetration enhancer |
| Brij 58 | 5% | solubilizer |
| PEG1000 | 10% | wetting agent |
| Carbopol 980 | 0.5% | gel-forming agent |
| NaOH solution 10% | 1% | precipitating agent |
| Silicone 0.65 cSt | 5% | siloxane coating agent |
| Silicone Cyclomethicone 5-NF | 5% | siloxane coating agent |
| Purified water | ad 100% | base, solvent |

Properties:

White gel of excellent consistency with menthol odour and with a membrane penetration (cumulative, 6 hours) of 478 micrograms/square cm.

Evaluation:

A gel containing the active ingredient is suspended form. It can be easily manufactured on an industrial scale. The membrane penetration is immediate the consistency and organoleptic properties are excellent.

Comparative examples 1 and 2 are experiments with gels, which are closely tailored to the approach taken in WO2009007764 and WO2010089617.

Comparative Example 1

Composition:

| Celecoxib | 3% | active ingredient |
|---|---|---|
| Carbopol 980 | 0.5% | gel-forming agent |
| NaOH solution 10 (w/v) % | 1% | precipitating agent |
| Silicone 0.65 cSt | 3.3% | siloxane coating material |
| Silicone 100 cSt | 10% | siloxane coating material |
| Purified water | ad 100% | base, solvent |

Features:

Easily spreadable, odourless, non-sticking gel, with a cumulative penetration (6 hours) 3.1 micrograms/square cm.

Evaluation:

A classic, stable gel, which can be easily manufactured. Although the gel can be easily used and is of good consistency, the skin penetration is poor.

Comparative Example 2

| Celecoxib | 3% | active ingredient |
|---|---|---|
| Carbopol 980 | 0.5% | gel-forming agent |
| NaOH solution 10 (w/v) % | 1% | precipitating agent |
| Silicone 0.65 cSt | 10% | siloxane coating material |
| Silicone 100 cSt | 1% | siloxane coating material |
| Purified water | ad 100% | base, solvent |

Features:

Easily spreadable, odourless, non-sticking gel with a cumulative penetration (6 hours) of 4.8 micrograms/square cm.

Evaluation:

A classic, stable gel which can be easily manufactured. Although the gel can be easily used and of good consistency, the skin penetration is poor.

Conclusions from Experiments Above:

The penetration of the active ingredient can be somewhat increased by varying the amounts of the siloxane ingredients, but the desired range cannot be achieved.

Comparative example 3 takes the approach of enhancing the penetration of celecoxib using menthol along with various solubilizers. The mixture of celecoxib and menthol was found to dissolve in most solubilizers tested (comparative example 3 provides the embodiment with Tween 60), but only those having a high HLB value can maintain it in the aqueous phase. None of the solubilizers were found to be suitable for forming an emulsion alone in these experiments, since the active ingredient starts crystallizing instantly Using a complex emulgent (high+low HLB solubilizers), an emulsion can be formed which crystallizes after a few hours. The solution is stable on the short term (24 hours) only.

Comparative Example 3

Composition:

| Celecoxib | 3% | active ingredient |
|---|---|---|
| Menthol | 3% | fragrance, penetration enhancer |
| Tween 60 | 12% | solubilizer |
| Ethanol | 10% | solubilizer |
| Carbopol980 | 0.5% | gel-forming agent |
| NaOH solution 10% | 1% | precipitating agent |
| Silicone 0.65 cSt | 5% | siloxane ingredient |
| Purified water | ad 100% | base, solvent |

Features:

A yellowish, honey-like, viscous, sticky gel with a membrane penetration (6 hours) of 2341 micrograms/square cm.

Evaluation:

The manufacture of this composition is easily feasible. The in vitro penetration is excellent. However, the physical state, consistency and applicability of the gel is poor.

On the basis of the above composition of comparative example 3, further similar compositions were prepared by varying the amount of the active ingredient, from 3-6%, the amount of menthol from 1-2% and the amount of Tween 60 from 12-24%, each time using 1% Carbopol to obtain a suitable gel consistency.

The membrane penetration increases with increasing active ingredient content but not proportionally. Increasing viscosity of the gel significantly degrades membrane penetration.

In the composition of comparative example 3 and in those based thereon, crystallization was observed after 3-4 days of storage.

The preceding examples can be repeated with similar success by substituting the generically or specifically described reactants and/or operating conditions of this invention for those used in the preceding examples.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

From the foregoing description, one skilled in the art can easily ascertain the essential characteristics of this invention and, without departing from the spirit and scope thereof, can make various changes and modifications of the invention to adapt it to various usages and conditions.

The entire disclosures of all applications, patents and publications cited herein are incorporated by reference herein for the disclosure of materials mentioned herein regarding said applications, patents and publications.

The invention claimed is:

1. A gel composition comprising:
a selective COX-2 inhibitor compound in micronized particulate form, the selective COX-2 inhibitor comprising about 1.5 to 4.0% of the composition, the selective COX-2 inhibitor coated with a volatile siloxane agent prior to addition to the gel composition, the volatile siloxane agent configured to act as a barrier against dissolution of the selective COX-2 inhibitor compound until application to a body surface;
a penetration enhancing compound, comprising menthol comprising about 0.75% to 2.0% of the composition;
a solubilizer, comprising poly(ethylene glycol)-block-poly(propylene glycol)-block-poly(ethylene glycol) comprising about 4.0% of the composition;
a wetting agent, comprising polyethylene glycol 1000 comprising about 10% of the composition;
a gel forming agent;
a precipitating agent;
a solvent; and
wherein the volatile siloxane agent comprises hexamethyldisiloxane and decamethylcyclopentasiloxane, the volatile siloxane agent comprising about 10% of the composition.

2. The composition of claim 1, wherein the composition is in the form of a suspension gel.

3. The composition of claim 1, wherein the composition is partially in the form of a solution gel, wherein at least a portion of an active compound is dissolved in the gel.

4. The composition of claim 1, which when applied to the skin, provides for the membrane penetration of the COX-2 inhibitor in the amount of at least 400 micrograms/sq. cm in 6 hours.

5. The composition of claim 1, further comprising a second solubilizer, wherein the solubilizers together have a hydrophilic-lipophilic balance (HLB) value above 10.

6. The composition of claim 1, wherein the COX-2 inhibitor is celecoxib, deracoxib, valdecoxib or rofecoxib.

7. The composition of claim 1, which contains by weight percent

| | |
|---|---|
| Celecoxib | 2% |
| Menthol | 1% |
| Polymerized prop-2-enoic acid ester | 0.5% |
| NaOH aqueous solution (10 m/v %) | 1% |
| Hexamethyldisiloxane | 5% |
| Decamethylcyclopentasiloxane | 5% |
| Purified water | ad 100%. |

8. A process for preparing a composition of claim 1, comprising
- swelling the gel forming agent in the solvent, and neutralizing with the precipitating agent until reaching a pH of from about 5.5 to about 7.5, warming up the solubilizer to approximately 50° C. and dissolving therein the wetting agent and the penetration enhancing compound,
  - thereby forming a melt,
  - stirring the melt into the gel,
  - then mixing together the volatile siloxane agents,
  - dispersing the selective COX-2 inhibitor compound, into the volatile siloxane agent and homogenized, optionally by a colloid mill, thereby forming a suspension, and
  - stirring the suspension into the gel and homogenized, optionally by a colloid mill,
  - wherein the process includes the interchanging of the penetration enhancing compound and the selective COX-2 inhibitor compound in the above process steps.

9. A process for preparing a composition of claim 7, comprising
- swelling the polymerized prop-2-enoic acid ester in the water and neutralizing by the NaOH solution until reaching a pH of from about 5.5 to about 7.5,
- thereby forming a gel
- warming the poly(ethylene glycol)-block-poly(propylene glycol)-block-poly(ethylene glycol) and polyethylene glycol 1000 up to approximately 50° C. and dissolving menthol in their mixture, thereby forming a melt,
- stirring the melt into the gel,
- mutually dissolving the hexamethyldisiloxane and the decamethylcyclopentasiloxane by mixing them together,
- dispersing the micronized celecoxib in the mixture of the hexamethyldisiloxane and the decamethylcyclopentasiloxane and homogenizing, optionally by a colloid mill, thereby forming a suspension, and
- stirring the suspension into the gel and homogenizing, optionally by a colloid mill,
- wherein the process includes the interchanging of the menthol with the celecoxib in the above process steps.

10. A process for preparing a composition of claim 1, comprising swelling the gel forming agent in the solvent, optionally neutralizing with the precipitating agent until reaching a pH of from about 5.5 to about 7.5,
- warming up the solubilizer to approximately 50° C. and dissolving therein the wetting agent, the COX-2 inhibitor active ingredient
- and the penetration enhancing compound,
- thereby forming a melt,
- stirring the volatile siloxane agent into the gel and homogenizing, and
- stirring the melt obtained from said solubilizer, wetting agent, active ingredient and
- penetration enhancing compound into the gel and homogenized, optionally by a colloid mill.

11. A method for treating inflammation, colorectal polyps, menstrual cramps, sports injuries, osteoarthritis, rheumatoid arthritis, pain and acute pain, and for reducing the risk of peptic ulceration, comprising administering an effective amount of a composition of claim 1 topically to a patient in need thereof.

12. The composition of claim 1, wherein the penetration enhancing compound is present within the volatile siloxane coating of the selective COX-2 inhibitor compound.

13. The composition of claim 1, wherein the weight ratio between the hexamethyldisiloxane and the decamethylcyclopentasiloxane is about 1:1.

14. A pharmaceutical composition for application to the skin, comprising:

celecoxib comprising about 1.5-5% of the composition;

polymerized prop-2-enoic acid ester comprising about 0.3-1% of the composition;

menthol comprising about 1-2% of the composition;

poly(ethylene glycol)-block-poly(propylene glycol)-block-poly(ethylene glycol) comprising about 4% of the composition;

polyethylene glycol 1000 comprising about 10% of the composition;

hexamethyldisiloxane comprising about 5% of the composition;

decamethylcyclopentasiloxane comprising about 5% of the composition;

NaOH to bring the composition to a pH of from about 5.5 to about 7.5; and purified water.

15. The composition of claim 14, wherein the celecoxib is coated in the hexamethyldisiloxane and the decamethylcyclopentasiloxane prior to addition to the composition.

* * * * *

UNITED STATES PATENT AND TRADEMARK OFFICE
CERTIFICATE OF CORRECTION

PATENT NO. : 10,045,935 B2
APPLICATION NO. : 13/562686
DATED : August 14, 2018
INVENTOR(S) : Endre Mikulásik et al.

Page 1 of 1

It is certified that error appears in the above-identified patent and that said Letters Patent is hereby corrected as shown below:

In the Specification

In Column 2, Line 9 (Approx.), change "459-- - 471.]," to --459-471.],--

In Column 2, Line 46, change "penentration" to --penetration--

In Column 3, Line 49, change "10," to --10.--

In Column 5, Line 41, change "penetration" to --penetration".--

In Column 5, Line 54, change "cosmoceuticals" to --cosmeceuticals--

In Column 7, Line 34, change "SNF." to --5NF.--

In Column 7, Line 37, change "on" to --one--

In Column 7, Line 43, change "stifling" to --stirring--

In Column 10, Line 32 (Approx.), change "Using" to --using--

Signed and Sealed this
Twentieth Day of November, 2018

Andrei Iancu
*Director of the United States Patent and Trademark Office*